United States Patent [19]
Pierfitte et al.

[11] Patent Number: 5,105,086
[45] Date of Patent: Apr. 14, 1992

[54] GAMMA CAMERA EQUIPMENT HAVING TWO DETECTOR HEADS

[75] Inventors: Michel Pierfitte, Villepreux; Christian Pare, Plaisir; Francois de la Barre, Sevres, all of France

[73] Assignee: Sopha Medical, Paris, France

[21] Appl. No.: 606,934

[22] Filed: Oct. 31, 1990

[30] Foreign Application Priority Data

Nov. 2, 1989 [FR] France ................... 89 14356

[51] Int. Cl.⁵ ................. G01T 1/163; G01T 1/166
[52] U.S. Cl. ............... 250/363.08; 250/363.02; 250/363.05
[58] Field of Search ............ 250/363.08, 363.02, 250/363.04, 363.05; 378/189; 128/653 R, 659

[56] References Cited

U.S. PATENT DOCUMENTS

| | | | |
|---|---|---|---|
| 3,654,465 | 4/1972 | Platz et al. | 250/363.08 X |
| 4,645,933 | 2/1987 | Gambini et al. | 250/363.08 X |
| 4,651,007 | 3/1987 | Perusek et al. | 250/363.08 |
| 4,943,726 | 7/1990 | Plummer | 250/363.02 |
| 4,982,416 | 1/1991 | Pare et al. | 378/20 |

FOREIGN PATENT DOCUMENTS

| | | |
|---|---|---|
| 0049562 | 4/1982 | European Pat. Off. . |
| 0251487 | 1/1988 | European Pat. Off. . |
| 0320741 | 6/1989 | European Pat. Off. . |
| 2323710 | 11/1974 | Fed. Rep. of Germany . |

*Primary Examiner*—Constantine Hannaher
*Assistant Examiner*—Edward J. Glick
*Attorney, Agent, or Firm*—Oblon, Spivak, McClelland, Maier & Neustadt

[57] ABSTRACT

Gamma camera equipment of the invention has two detector heads capable of being associated for whole body type examination in which the two detector heads co-operate, or else of being separated for tomographic type examination, where only one of the heads is in use nevertheless continuing to be powered. In order to reinforce the mechanical cohesion of the assembly, the lower detector head is displaceable on rails which are fixed to the stand on which the upper head is mounted so that the stand constitutes a counterweight for the lower head, with struts being provided at the end of the rails only. The invention is particularly suitable for making compact multi-analysis equipment suitable for installation on any type of floor.

16 Claims, 2 Drawing Sheets

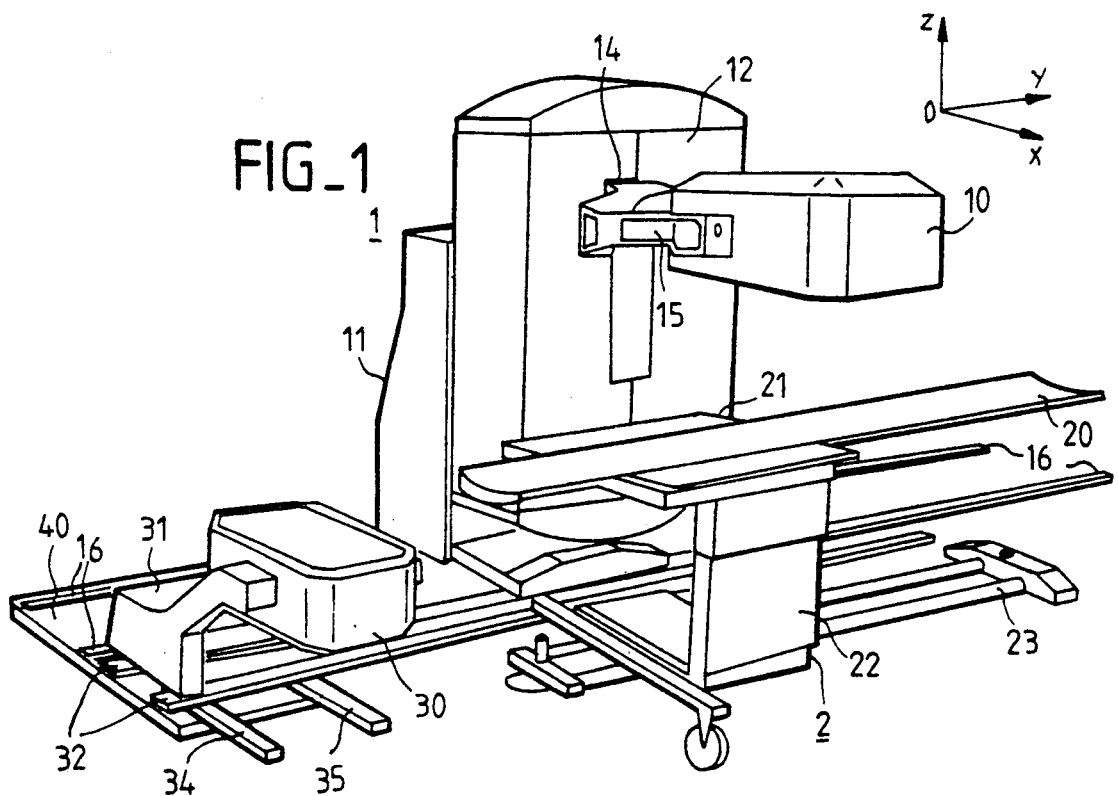
FIG_1
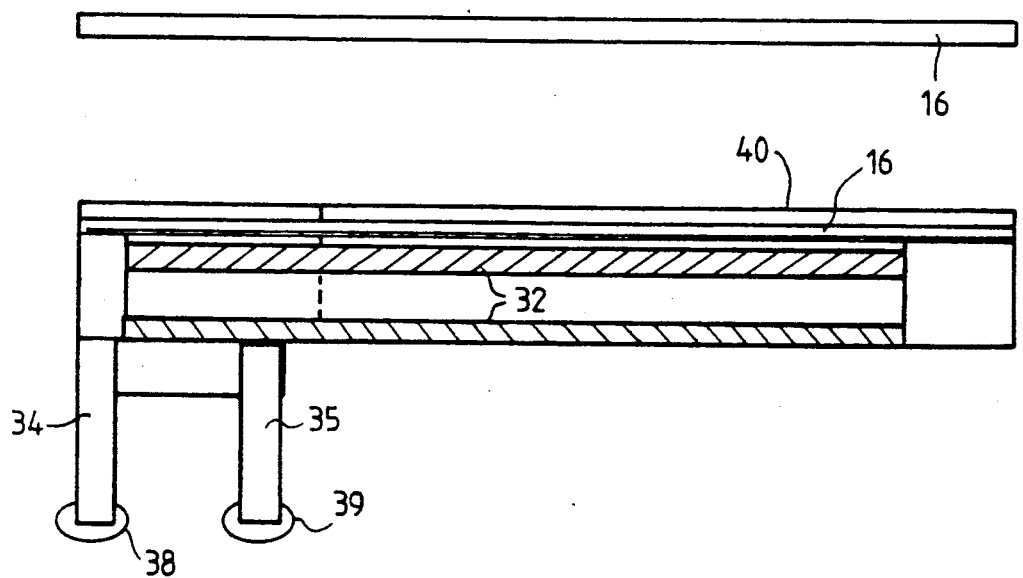
FIG_2

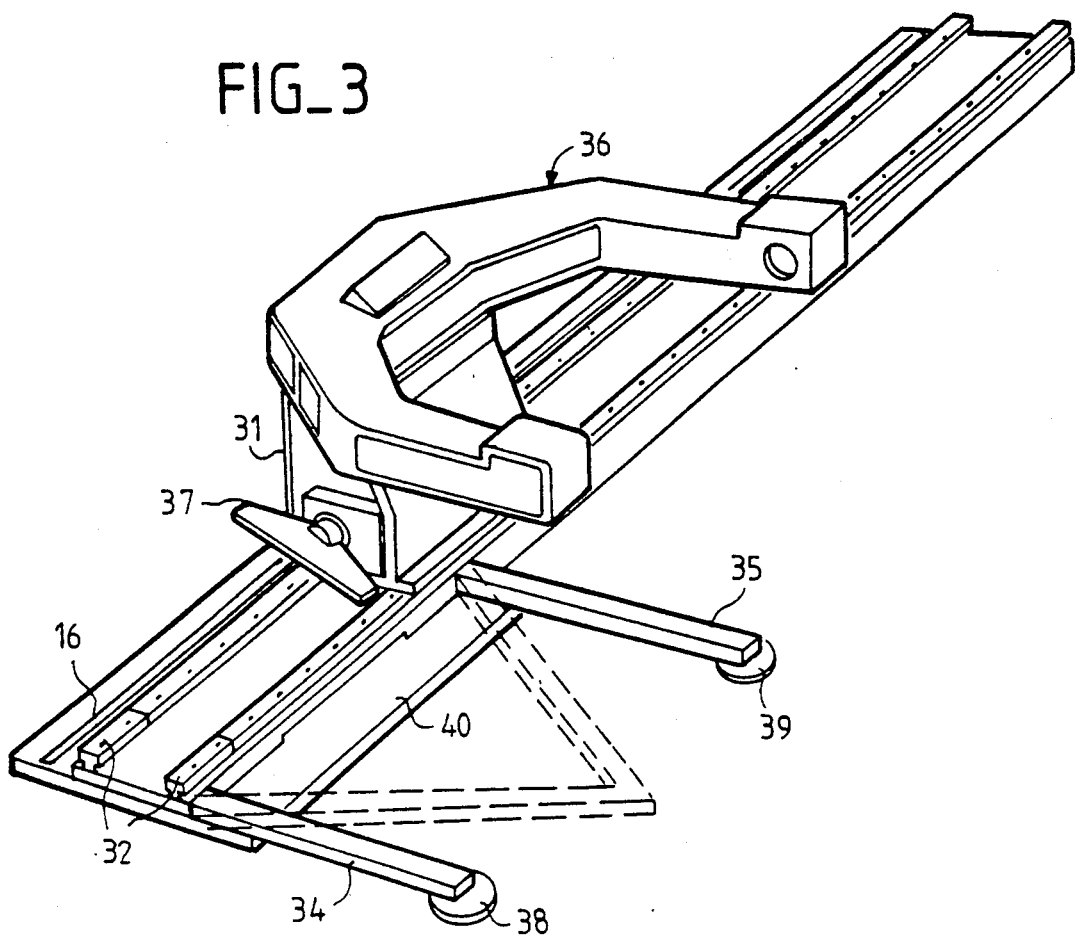
FIG_3
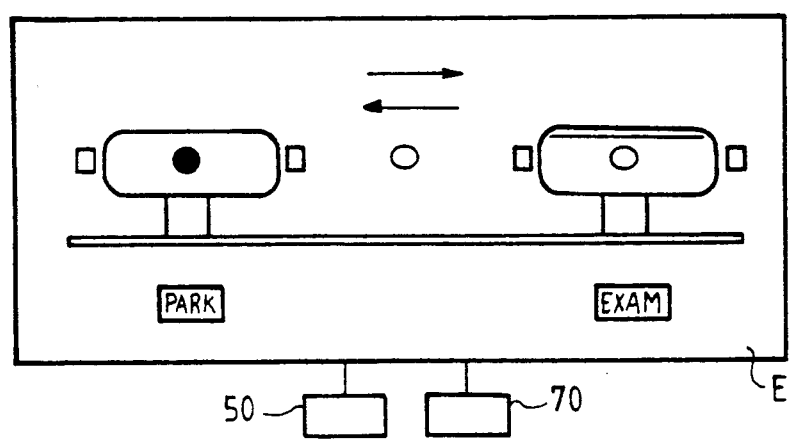
FIG_4

GAMMA CAMERA EQUIPMENT HAVING TWO DETECTOR HEADS

FIELD OF THE INVENTION

The invention relates to gamma cameras or scintigraphy cameras, and more particularly it relates to gamma camera equipment having two detector heads.

BACKGROUND OF THE INVENTION

Conventionally, equipment for medical examination by scintigraphy is adapted either to so-called "tomographic" analysis or else to so-called "whole body" analysis. For tomographic analysis, a detector head including a gamma radiation collimator, a scintillator, and an associated detector assembly are rotated around the patient so as to form images in different planes of an organ under observation.

For whole body analysis, two camera heads are disposed respectively above and below a special patient-carrying bed, enabling plane images parallel to the inlet faces of the heads to be formed from the radiation received by the two heads. Conventionally, in an examination of this type, both heads are displaced simultaneously, with the head situated above the patient bed being displaced parallel to the bed simultaneously with the stand as a whole, while the head situated beneath the patient bed being displaced on rails that are held on the floor by a strut means extending over the entire length of the rails. Such an installation is heavy and cumbersome and yet nevertheless does not provide for flexible utilization of the equipment. In particular the detector heads are specialized: either a single head mounted to enable a wide range of rotary displacements to be performed in tomographic analysis; or else two coupled-together heads for longitudinal displacement in whole body analysis.

SUMMARY OF THE INVENTION

The object of the invention is to provide gamma camera equipment of a structure which is simpler than prior equipment, and which also makes it possible to perform either tomographic analysis or whole body analysis as selected by an operator while using only two distinct detector heads.

According to the invention, the gamma camera equipment comprises a stand having a first detector head mounted thereon, and a low second detector head, and the equipment is characterized in that in order to enable it to perform two types of examination: whole body type examination using both detector heads and tomographic type examination using only the first detector head. The equipment includes running rails on which the second detector head is capable of being displaced between an active position where its support is locked to the stand, and a standby position where its support is locked to the running rails, the standby position being at the end of the rails, the second head being powered, regardless of its position, whenever the first head is powered.

As mentioned above, this equipment includes a detector head which is disposed permanently above the special bed and which is capable of rotating in a tomographic analysis mode, and a second camera head which is displaceable on rails fixed to the floor so as to occupy either a standby position at the end of the rails when the equipment is operating in the tomographic mode, or else to be brought beneath the special bed by running along the rails in a whole body analysis mode.

A problem with this type of equipment relates to the fact that a gamma camera head constitutes a heavy assembly, weighing about 400 kg, and that the second head, when on standby at the end of the rails, needs to be continuously powered and, being in a cantilevered position, must be associated with a mechanical assembly which is strong enough to avoid any danger of breakage, in particular of being torn off.

This problem could be solved as in prior art two head whole body analysis equipment by providing a strut extending over the entire length of the rails on which the second head is displaced. However this increases the area of floor occupied by the equipment. Alternatively, strong anchor points are provided, thereby requiring the floor to be strong and compact, which is rarely the case. Another object of the invention is thus to provide gamma camera equipment having two detector heads in which the mechanical assembly associated with the second head prevents the second head from being torn off while on standby, and is simpler while nevertheless being satisfactory; in addition, this equipment is suitable for installation on any kind of floor, and even, should the need arise, on a floating floor.

The invention also provides equipment in which the running rails on which the second head is displaceable are fixed to a connection plate on which the weight of the stand is also exerted, the stand carrying the first detector head thus constituting a counterweight for the second detector head.

BRIEF DESCRIPTION OF THE DRAWINGS

An embodiment of the invention is described by way of example with reference to the accompanying drawings, in which:

FIG. 1 is an overall view of gamma camera equipment of the invention;

FIG. 2 is a diagram of the floor space occupied by the various components constituting the gamma camera equipment of the invention;

FIG. 3 is a more detailed diagram of the mechanical assembly associated with the second detector head; and FIG. 4 shows the system for displaying the positions of the second detector head.

DETAILED DESCRIPTION

The gamma camera equipment of the invention as shown in FIG. 1 comprises a conventional assembly defined in a frame of reference (OX, Y, Z).

The gamma camera equipment feature a stand 1, i.e. a solid heavy and stable support column comprising a rear portion a support 12 capable of rotating in a vertical plane (YOZ), and an arm 14 fixed thereto and terminated by a fork 15. This fork 15 bears a first detector head 10 which turns about an axis (parallel to OY) defined by the fixation points of the first detector head 10 to the fork 15. The stand is optionally displaceable on rails 16 in a direction OY together with the head it supports;

Also, the gamma camera equipment has an examination table 2 comprising a bed 20 which is cantilevered out from a support 21 which is itself cantilevered out from a leg 22 so as to enable a second detector head to be disposed beneath the bed. The bed is made of a material which is transparent to the gamma radiation used for examination purposes. The leg 22 on which the bed is supported is slidably mounted on rails 23 fixed to the floor and extending parallel to the axis OY.

Also shown is a second detector head 30 which is cantilevered out from a support 31, the second head assembly having a mass of about 400 kg and being displaceable at floor level on rails 32.

These rails 32 are preferably fixed to the stand 1 so that the stand constitutes a counterweight for the second detector head. Because the second head is cantilevered out, when it is in its standby or "parked" position at the end of the rail 32, struts 34 and 35 are provided at that end only of the rail 32 in order to prevent dislodging. In order to prevent any play, the struts are welded to a base plate 40 which also carries the running track for the front wheel of the stand 1, and the rails 32 for the second head. This compact assembly can be installed on any type of floor and does not require fixing in a particularly rigid manner, with the stand carrying the first head then constituting the counterweight for the cantilevered-out second detector head. While the second detector head 30 is in its standby position, and even though it is always powered whenever the first head is powered, it is additionally locked onto the rails 32. While it is in its active position, the second head is unlocked from the rails but is then locked to the stand 1.

FIG. 2 is a diagram showing the floor space occupied by the multi-analysis gamma camera equipment of the invention, and in the vicinity of the examination table 2. When the same references are used as in FIG. 1, they designate the same items, namely 16 for the guide rails for the stand assembly and its first detector head, 32 for the ball rails for guiding the support assembly 31 and the second detector head, and 34 and 35 for the struts disposed at the end of the rails 16. These various items are carried by the base plate 40.

FIG. 3 shows in greater detail the mechanical assembly associated with the second detector head (not shown in this figure in order to show the other items more clearly). In particular, there can be seen a fork 36 for carrying the second detector head 30, the fork 36 being mounted on a support 31 which contains the power supply for the detector, a pedal 37 for locking and unlocking the support relative to the rails 32, and the struts 34 and 35 which are welded to the base plate 40 which is common to the rails 32 and to the running track 16 for the front wheel of the stand. The stand assembly carrying the first detector head has a mass of about 900 kg while the support 31 together with the second detector head has a mass of about 400 kg.

The assembly is thus balanced by the facts that: the base plate is fixed to the floor; half of the weight of the stand is exerted on the base plate 40 via its front wheel bearing on the corresponding running track formed on the base plate; and the struts which are welded thereto exert reaction on the floor preventing the second head from tipping over by dislodging the rails when the second head is in its standby position, i.e. when the stand is at the other end of the rails.

Naturally, in the embodiment shown, a single base plate is used. It is perfectly possible to use two different base plates for the stand running track and for the rails carrying the second detector head, but under such circumstances the two plates must be interconnected by a fixed connection component. Again the tipping reaction must be exerted via the second head being locked to the stand.

In order to enable the assembly to be properly balanced, the struts 34 and 35 are provided with respective adjustment jacks 38 and 3 for adjusting the height of the struts above the floor. In FIGS. 1 to 3, the struts are shown as extending orthogonally to the direction in which the rails 32 extend. In practice, the system of struts used for preventing the ends of the rails from being dislodged could also be constituted by two angled struts interconnected at a common point where a single jack is provided for adjusting height relative to the floor, and this disposition is shown in dashed lines in FIG. 3.

This organization clearly has the advantage of occupying less floor area. In both cases, whether the struts are orthogonal or angled, the weld zones between the struts and the base plate are sufficiently far apart to be on opposite sides of the support 31 when second detector head 30 in its standby position on the rails 32. If necessary, for avoiding transmitting vibrations in regions which are frequently subjected to earthquakes, the base plate 40 may be an antiseismic base plate.

The locking means for the support 31 carrying the second detector head 30 are shown as being constituted by a pedal actuating a locking system. The locking system includes a mechanical member which extends into the stand and also into the second head (for whole body examination) or else into the stand and the rails 32 or the base plate 40 (for tomographic applications). This member is long enough to be capable of engaging in all three simultaneously when going from one configuration to another. A retaining spring may be used for locking it in one direction or the other. An electrical safety system may be associated therewith so that the equipment recognizes proper locking, both when in the active position of the stand and when in the standby position on the rails 32, and a system may also be provided for displaying an end-of-stroke position. One embodiment of such a display system is shown in FIG. 4. A display screen E has a certain number of symbols permanently displayed thereon, and in particular the active position of the bottom detector head which is marked "EXAM", the standby position of the lower detector head which is marked "PARKED", and a representation of the path over which this head may be displaced. Indicator lamps are provided to show the real position of the lower head within the equipment. The lamps in the centers of the two positions are red or green depending on the position of the head, with green indicating that the head is locked either to the stand I (the "EXAM" active position), or else on the rails 32 (the standby position "PARKED"), with an orange intermediate lamp between these two positions indicating that the lower head is moving. Connectors 50, 70 provide a connection with the systems for locking respectively to the stand and to the rails.

The invention is not limited to the embodiment described and shown. In particular, the invention is applicable to any equipment having two detector heads and being capable of performing either tomographic analyses using one head or else whole body analyses using both heads as selected by an operator and depending on the position occupied by the lower detector head.

We claim:

1. Gamma camera equipment having two detector heads comprising firstly a stand on which a first detector head is mounted, and secondly a lower, second detector head, wherein in order to enable two types of examination to be performed, namely whole body type examination using both detector heads simultaneously and tomographic type detection using only the first detector head, the equipment includes running rails on which the second detector head is capable of being moved between an active position and a standby position at the end of the rails, and means for moving said second detector head along said running rails, said second head, regardless of the position it occupies, always being powered whenever the first head is powered.

2. Equipment according to claim wherein the running rails on which the second detector head is displaceable are fixed to a connection plate on which the weight of the stand is also exerted, the stand constituting a counterweight for the second detector head.

3. Equipment according to claim 2, wherein a base plate carries both a running track for the stand and the running rails for the second detector head, thus forming a connection plate.

4. Equipment according to claim 2, wherein the second detector head is cantilevered out from a support which is displaceable on the rails, and a system of struts is provided at the end of the rails for balancing the second detector head when in its standby position.

5. Equipment according to claim 4, wherein the system of struts comprises two struts extending orthogonally to the direction in which the rails extend, the spacing between the struts being not less than the length on the rails of the support.

6. Equipment according to claim 4, wherein the system of struts comprises two struts extending at an angle relative to the direction of the rails, the struts being interconnected in a common zone.

7. Equipment according to claim 1, wherein a display system is provided in the equipment for displaying the position of the lower second head.

8. Gamma camera equipment having two detector heads and comprising firstly a stand on which a first detector head is mounted, and secondly a lower, second detector head, wherein in order to enable two types of examination to be performed, namely whole body type examination using both detector heads simultaneously and tomographic type detection using only the first detector head, the equipment includes running rails, lying on the ground, on which the second detector head is capable of being moved between an active position and a standby position at the end of the rails, and means for moving said second detector head along said running rails, said running rails on which the second detector head is displaceable being fixed to a connection plate, also lying on the ground, on which the weight of the stand is also exerted, the stand constituting a counterweight for the second detector head by means of a locking member for mechanically locking temporarily said stand to said second detector.

9. Gamma camera equipment having two detector heads which can enable tow types of examinations to be preformed, whole body examination in which both detector heads are used simultaneously and tomographic detection in which only the first detector head is used, comprising:
    a first detector head;
    a stand on which said first detector head is mounted;
    a second detector head mounted below said first detector head;
    running rails on which the second detector head is capable of being moved between an active position and a standby position, the standby position being at the end of the rails; and
    means for moving said second detector head along said running rails, said second detector head always being powered whenever the first head is powered regardless of a position the second detector head occupies.

10. The gamma camera equipment according to claim 9, further comprising a connection plate to which the running rails for the second detector head are fixed and on which the weight of the stand is also exerted, the stand thereby constituting a counterweight for the second detector head.

11. The gamma camera equipment according to claim 10, further comprising a base plate which carries both a running track for the stand and the running rails for the second detector head, thus forming the connection plate.

12. The gamma camera equipment according to claim 10, wherein the second detector head is cantilevered out from a support which is displaceable on the running rails, and a system of struts is provided at the end of the running rails for balancing the second detector head when it is in its standby position.

13. The gamma camera equipment according to claim 12, wherein the system of struts comprises two struts extending orthogonally to the direction in which the rails extend, a spacing between the struts being not less than the length on the rails of the support.

14. The gamma camera equipment according to claim 12, wherein the system of struts comprises two struts extending at an angle relative to the direction of the rails, the struts being interconnected in a common zone.

15. The gamma camera equipment according to claim 9, further comprising a display system for displaying the position of the second detector head.

16. The gamma camera equipment according to claim 9, wherein the running rails on which the second detector head is capable of being moved between an active position and a standby position at the end of the rails lies on the ground, said running rails being fixed to a connection plate also lying on the ground on which the weight of the stand is exerted, the stand thereby constituting a counterweight for the second detector head by means of a locking member for mechanically temporarily locking said stand to said second detector.

* * * * *